(12) United States Patent
Willoughby et al.

(10) Patent No.: US 9,192,626 B2
(45) Date of Patent: Nov. 24, 2015

(54) DENTAL USES OF SILVER HYDROSOL

(75) Inventors: Andrew J. M. Willoughby, Tsawwassen (CA); William D. Moeller, Alpine, UT (US)

(73) Assignee: AMERICAN SILVER, LLC, Alpine, UT (US)

( * ) Notice: Subject to any disclaimer, the term of this patent is extended or adjusted under 35 U.S.C. 154(b) by 847 days.

(21) Appl. No.: 12/482,359

(22) Filed: Jun. 10, 2009

(65) Prior Publication Data

US 2010/0316685 A1 Dec. 16, 2010

(51) Int. Cl.

| | |
|---|---|
| *A61Q 11/00* | (2006.01) |
| *A61K 33/38* | (2006.01) |
| *A61K 6/02* | (2006.01) |
| *A61K 6/04* | (2006.01) |
| *A61K 8/22* | (2006.01) |
| *A61K 9/08* | (2006.01) |
| *A61K 9/00* | (2006.01) |
| *A61K 33/40* | (2006.01) |
| *A61K 36/886* | (2006.01) |
| *A61K 45/06* | (2006.01) |
| *A61L 15/44* | (2006.01) |
| *A61L 15/46* | (2006.01) |

(52) U.S. Cl.
CPC ............... *A61K 33/38* (2013.01); *A61K 9/006* (2013.01); *A61K 9/0063* (2013.01); *A61K 33/40* (2013.01); *A61K 36/886* (2013.01); *A61K 45/06* (2013.01); *A61L 15/44* (2013.01); *A61L 15/46* (2013.01)

(58) Field of Classification Search
USPC .......... 424/613, 616, 617, 618; 433/215, 216, 433/217.1, 226
See application file for complete search history.

(56) References Cited

U.S. PATENT DOCUMENTS

| | | | | |
|---|---|---|---|---|
| 3,968,567 A | * | 7/1976 | Nevins ......................... | 433/224 |
| 4,446,140 A | * | 5/1984 | Nelson ......................... | 514/289 |
| 5,437,858 A | * | 8/1995 | Hungerbach et al. ........... | 424/53 |
| 5,945,032 A | * | 8/1999 | Breitenbach et al. .... | 252/186.29 |
| 6,153,210 A | * | 11/2000 | Roberts et al. ................ | 424/411 |
| 6,503,539 B2 | * | 1/2003 | Gestrelius et al. ............. | 424/549 |
| 6,582,713 B2 | * | 6/2003 | Newell et al. ................. | 424/407 |
| 7,351,684 B2 | * | 4/2008 | Tichy et al. ................... | 510/372 |
| 2003/0124482 A1 | * | 7/2003 | Calvert .......................... | 433/81 |
| 2004/0258738 A1 | * | 12/2004 | Kania et al. ................... | 424/443 |
| 2005/0036955 A1 | * | 2/2005 | DeGould ........................ | 424/53 |
| 2006/0182813 A1 | * | 8/2006 | Holladay ....................... | 424/618 |
| 2006/0240381 A1 | * | 10/2006 | Rizoiu et al. .................... | 433/80 |

FOREIGN PATENT DOCUMENTS

| | | |
|---|---|---|
| KR | 100802343B B1 | 4/2008 |
| WO | WO 02/085299 A1 | 10/2002 |
| WO | WO 2005/000324 | 1/2005 |

OTHER PUBLICATIONS

Rai, M. et al., "Silver Nanoparticles as a new generation of antimicrobials." Biotechnology Advances. 27 (2009) pp. 76-83. Sep. 30, 2008.
Li, Y. et al., "Antimicrobial effect of surgical masks coated with nanoparticles." J Hospital Infection. 62 (2006) pp. 58-63. Aug. 15, 2005.
Zheng, et al. "The use of BMP-2 coupled Nanosilver PLGA composite grafts to induce bone repair in grossly infected segmental defects." Biomaterials. 31 (2010) pp. 9293-9300. Sep. 22, 2010.
United States Environmental Protection Agency, Peracetic Acid Results http://www.epa.gov/opptintr/aegl/pubs/results80.htm.
Peroxyformic acid, LookChecm.Com http://www.lookchem.com/Peroxyformic-acid/.
Peracetic acid—Wikipedia,the free encyclopedia http://en.wikipedia.org/wiki/Peracetic_acid.

\* cited by examiner

*Primary Examiner* — Lezah Roberts
(74) *Attorney, Agent, or Firm* — Venable LLP; Stefan J. Kirchanski (57) ABSTRACT

Microbiologically effective silver hydrosol is used to reduce the local level of microorganisms at the site of a dental procedure and to prevent or inhibit their growth during the healing that follows the procedure. Any gingival lesions created by a dental procedure are treated with silver hydrosol in an aqueous gel. Following the procedure the patient's mouth is periodically rinsed several times a day with a solution of silver hydrosol or, more preferably, with a combination of silver hydrosol and hydrogen peroxide. These steps result in a significant reduction in post operative pain and swelling. Overall healing is accelerated by this treatment.

22 Claims, 2 Drawing Sheets

DENTAL USES OF SILVER HYDROSOL

CROSS-REFERENCE TO PRIOR APPLICATIONS

N/A

U.S. GOVERNMENT SUPPORT

N/A

BACKGROUND OF THE INVENTION

1. Area of the Art

The present application is in the area of dental surgery and procedures and more particularly methods for minimizing pain, swelling and/or infection(s) following various dental procedures.

2. Description of the Background Art

Solid silver and silver compounds have a long history in human health. Silver implements (silverware) were long believed to have beneficial effects. The therapeutic use of silver dates at least as far back as 1647 when it was prescribed for the treatment of epilepsy. Syphilis was treated with silver arsepenamine (silver arsenic compound) in the early twentieth century, but the advent of antibiotics and related antimicrobial agents largely replaced the use of metals as anti-infective agents. However, ophthalmic silver nitrate solutions are still used to treat the eyes of neonates. Other topical silver-containing solutions are employed primarily for treatment of burn wounds or hard to heal sores. For example, topical silver sulfadiazine has been used in burn treatments for many years. Silver ions are also implanted into catheters and other medical devices to prevent local infection. There is considerable confusion concerning the form of silver that is effective (i.e., ionic [silver salt] versus elemental silver).

Certainly, silver salts such as silver nitrate are known to be antimicrobial. It also appears that silver metal, at least in fine particulate form can also be effective. This may be due to the extensive surface area of such particles or it may be due to the release of or transient presence of ionic silver on such particles. A colloid is a type of mixture where one substance is dispersed evenly throughout another. When solid particles such as silver particles are dispersed in a liquid the colloid or colloidal suspension is known as a sol (hydrosol when the liquid is water). Many colloids (including silver sol) have the appearance of true solutions. In a true colloid the dispersed particles have at least one dimension between one nanometer ($1 \times 10^{-9}$ meters) and one micrometer ($1 \times 10^{-6}$ meters). Such particles are normally invisible even to a normal light microscope. We have gone through this explanation because the marketplace is filled with various types of colloidal silver products. "Colloidal silver" generally refers to suspensions of colloidal silver (metal) particles. However, there is confusion because silver salts have also been compounded with colloidal protein (gelatin) which solutions are also called "colloidal silver;" clearly such a gelatin product is quite different from silver hydrosol—the materials used in the present invention.

Silver hydrosols at silver concentrations less than about 50 ppm are produced by electrolytic processes (see for example U.S. Pat. No. 6,214,299 which is incorporated by reference in its entirety). Silver hydrosols with higher concentrations of silver are generally produced chemically from silver salts. It is believed that such chemically produced silver particles have different physical and chemical properties than those produced electrolytically. Concentrations of electrolytic silver particles at five parts per million or higher have been found in credible studies to kill numerous species of infectious bacteria and other microorganisms while showing very low toxicity to human tissues. For details see U.S. Pat. No. 7,135,195 which is incorporated by reference in its entirety.

SUMMARY OF THE INVENTION

The remarkable ability of certain silver hydrosol products to kill microorganisms and prevent their multiplication allows improved dental procedures that reduce pain and swelling and promote healing. A continuing problem in dental surgery and other dental procedures is the presence of an extensive bacterial flora in the human mouth. This has been dealt with by administering antibiotics systemically prior to and after dental procedures. Such antibiotic treatment may prevent systemic infections, but circulating antibiotics are not always able to prevent local infections at the site of the dental procedure. Even where obvious infections are avoided there is often considerable pain and swelling post operation. Silver hydrosol can even be included in surgical masks worn by dental personnel thereby limiting the transmission of disease organisms.

Our method uses microbiologically effective silver hydrosol (specifically ones produced according to U.S. Pat. No. 6,214,299) to reduce the local level of microorganisms at the site of a dental procedure and to prevent or inhibit their growth during the healing that follows the procedure. We disinfect the site of the procedure with a silver hydrosol or with a combination of silver hydrosol and hydrogen peroxide (a well known disinfectant). During the procedure the site is coated with liquid silver hydrosol—preferably in the form of an aqueous gel to prevent the silver from being washed away by saliva. Following the procedure the patient's mouth is periodically cleaned with silver hydrosol or, more preferably, with a combination of silver hydrosol and hydrogen peroxide.

When this disinfecting rinse is repeated several times a day for ten days or so, the speed of healing appears to be significantly improved. The duration of post operative pain and swelling is also significantly reduced implying that part of the "normal" pain and swelling (inflammation) is actually a result of a localized immune response to low grade infection. Consistent with this is the discovery that our silver hydrosol methods are synergistic with the use of oral antibiotics in that speed of healing and reduction of pain is more pronounced when the silver hydrosol method and oral antibiotics are used together as compared to either treatment by itself. While it was previously known that silver hydrosol is an effective antimicrobial, it was not known that silver hydrosol could produce dramatic and unexpected improvements in healing after dental procedures. Improvements that are not achievable with a wide variety of other antimicrobials that are current used or have been used in the past in dental treatments.

Silver hydrosol is particularly in disinfecting dental surfaces revealed during dental procedures. Silver hydrosol gel is advantageously applied to flaps of periodontal tissue and around the bone prior to suturing the tissue. Similarly it is effective when applied to tooth extraction sockets and to any gingival tissue wounded or exposed by a dental procedure. The disinfectant silver hydrosol rinse is also effective at disinfecting internal tooth surfaces exposed, for example, in the removal of decay or the remodeling of a tooth prior to the application of a crown or other type of dental restoration.

Silver hydrosol is also effective as a dental rinse for cleansing dental surfaces and for lowering bio-burden within a patient's mouth. Silver hydrosol is also an unexpectedly effective additive to a wide range of dental compositions where it imparts the compositions with disinfectant or antimicrobial properties. Often addition of antimicrobial drugs or typical chemical disinfectants is incompatible with a given dental composition. The silver particles within silver hydrosol are essentially chemically inert in that they rarely, if ever, interfere with the functioning of a dental composition.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide improved dental procedures and products.

We have developed significantly improved dental procedures based on the remarkable ability of certain silver hydrosol products to kill microorganisms and prevent their multiplication as well as to limit post operative pain and or swelling. As mentioned above, a continuing problem in dental surgery and other dental procedures is the presence of an extensive bacterial flora within the human mouth. This has led to the common practice of giving antibiotics (usually oral antibiotics) prior to and after dental procedures. While such antibiotics do appear to prevent systemic infections, circulating antibiotics are not always able to prevent local infections at the site of the procedure. Nor do antibiotics generally reduce pain and swelling post operation. Our method uses microbiologically effective silver hydrosol to reduce the local level of microorganisms at the site of a dental procedure and to prevent or inhibit their growth during the healing that follows the procedure. We disinfect the site of the procedure with silver hydrosol or with a combination of silver hydrosol and an aqueous solution of hydrogen peroxide (a well known disinfectant). During the procedure the site is coated with silver hydrosol—preferably in the form of a solution of an aqueous—gel to prevent the silver from being washed away by saliva. Following the procedure the oral cavity is periodically cleaned with silver hydrosol or, more preferably, with a combination of silver hydrosol and an aqueous hydrogen peroxide solution.

Alternatively, the silver hydrosol can be coated onto or impregnated into a variety of medical or dental devices and products to provide added antibacterial benefit (as will be further described below). We also demonstrate below that a variety of medical/dental devices (such as Collagen Matrix membranes, retraction cord and absorbable sutures can be soaked or hydrated in the silver hydrosol solution in order to provide increased antimicrobial activity. The goal of adding the silver hydrosol is to provide a continuous dynamic antimicrobial bacteriostatic environment capable of reducing bacterial bio-burden and thus post operative infection and inflammation. As will be detailed below, the results are dramatically better than those achieved with conventional antibiotic therapy or with repeated local disinfection in combination with hydrogen peroxide or other chemical disinfectants. It should be pointed out that prior to the present invention it was not known or anticipated that an antimicrobial could reduce inflammation.

The silver hydrosol used in our method is electrolytically produced silver produced according to the method of U.S. Pat. No. 6,214,299 and available from American Biotech Labs of Alpine, Utah. This material is produced according to the patented Silver Sol method in which each silver particle bears an electrical charge thereby ensuring continued suspension because the particles electronically repel each other. The charged silver particles are available as a suspension (hydrosol) in purified water, and this material is used in our method as an oral rinsing solution. The charged silver particles are also available in an aqueous gel herein referred to as "silver hydrosol gel (32 ppm)." The 32 ppm refers to the concentration of the silver metal present in the gel. The gel is a simple optically clear and colorless gel made from silver hydrosol, purified water and gelling ingredients (namely, carbo-vinyl acrylic polymer (carbomer), propylene glycol and triethanolamine (TEA)). These gelling ingredients are used in cosmetics; carbomer is a very high molecular weight polymer that is not absorbed by humans and is non-toxic. Other commonly commercially available gelling ingredients can obviously be substituted and/or added according to the present invention. The pH of this oral rinse may also be easily adjusted from neutrality to acid or alkaline conditions for the benefit of those individuals who have severe mouth odor (halitosis) due to overgrowth of sulfide producing bacteria. The oral rinse may also be combined with fluoride ions to help reduce the incidence of dental caries (tooth decay).

In addition to the above mentioned silver gel we also use silver hydrosol as a disinfecting rinse or surface disinfectant. We employ the silver hydrosol either alone or in combination with a dilute aqueous solution of hydrogen peroxide over a considerable range of concentrations. A mixture of silver hydrosol and aqueous hydrogen peroxide is stable. Hydrogen peroxide is generally used as a 3% aqueous topical solution for disinfecting tissue surfaces. The rinse solution described below is made by mixing equal volumes of 3% hydrogen peroxide solutions and 10 ppm silver hydrosol. Thus, the solution has an effective concentration of 1.5% hydrogen peroxide and 5 ppm silver. It is possible to use more concentrated hydrogen peroxide and more concentrated silver hydrosol to produce a rinse with up to 3% hydrogen peroxide (greater concentrations are believed to be irritating to tissue) and with 10 ppm or greater silver concentration. Mixtures with at least 1.5% hydrogen peroxide and at least 5 ppm silver are effective.

Intra-Oral Clinical Procedures and Clinical Findings from Use of Silver Hydrosol.

Oral Surgery: The following procedures required the surgical elevation of a full thickness flap of gingival periodontal tissue. Silver hydrosol gel (32 ppm) was applied underneath the full thickness flap and around the exposed bone prior to the flap and the underlying periosteum being repositioned and sutured back into place.

To test the effectiveness on surgical extraction of teeth 86 teeth were surgically removed from 64 different patients using a combination of a full thickness periodontal flap and/or bone removal, root/crown sectioning and forceps extractions. Silver hydrosol gel (32 ppm) was liberally applied around and directly into the fresh extraction sockets (immediately after tooth removal) as well as underneath the periodontal flap. This application was possible because the gel is essentially non-irritating and non-toxic—something which is not true of most ordinary chemical disinfectants. After the flap was sutured shut, more silver hydrosol gel (32 ppm) was then applied on top of the sutures and held in place by a cotton gauze pad for an additional 10-15 minutes. The antimicrobial nature of this silver hydrosol also gives rise to another practical dental application which is the coating or impregnation of this silver hydrosol solution into or onto the suture material such that it can also impart a further localized antibacterial affect on the surrounding sutured tissues which in turn promotes faster healing times and less inflammation.

Patients were then placed on a ten day regimen of three times daily mouth rinses with silver hydrosol 10 ppm combined (mixed) with 3% aqueous hydrogen peroxide solution to assist in disinfection and cleansing of the wound and the surrounding tissues. While hydrogen peroxide is generally an unstable compound and many materials cause it to break down rapidly, hydrogen peroxide is stable in the presence of silver hydrosol.

Clinical Results: All patients were all put on a post-operative recall program where they were followed up by phone at 24 and 72 hours and with a dental recall visit at 7-10 days and then again at 21-30 days. A total of 53 of our 64 patients successfully completed the entire recall program and of these, better than 92% experienced a marked decrease in both pain and swelling within the first 24-36 hours post operation. In fact, the majority of these compliant patients commented that they had not taken the prescription pain killers and anti-inflammatory medications we had prescribed them much beyond the first 24 hours after surgery. This is unusual because inflammation and pain may result in an increase of pain 24-36 hours post operation. From our clinical experience the above findings were highly unusual and directly attributable to the use of the silver products.

In one particular patient, eight molar teeth were surgically extracted in a single dental visit. Due to severe tooth decay and tortuous roots, extensive periodontal flaps were laid and major amounts of both the maxillary buccal plate and tuberosity as well as posterior mandibular bone were removed. As a result, of this surgery, extensive post operative periodontal defects were created. By all rights, the patient should have experienced significant swelling and post operative pain; however, with the liberal use of silver hydrosol gel (32 ppm) (at the time of the surgery) and a 10 day post operation. mouth rinse regimen using a combination of silver hydrosol 10 ppm silver hydrosol with 3% aqueous hydrogen peroxide solution we were very surprised to learn that the patient experienced only minor discomfort and very little post operative swelling. At 10 days post operation this patient's gingival tissues (around the surgical sites) looked surprisingly pink and firm (despite the obvious soft tissue defects) and there was virtually no red/edematous appearance to these tissues at all. In fact, the surgically impacted tissue(s) had the expected appearance of tissue 21 or so days post operation. From our clinical experience these results were highly unusual and directly attributable to the use of the silver products.

Placement of Dental Implants: To evaluate the effects of the silver products 19 dental implants were surgically implanted into 11 different patients using either Nobel Biocare or Zimmer Dental Implants. In three of these patients dental implants were placed concomitantly with the extraction of the teeth (immediate dental implantation) and in two of these three patients a bone augmentation procedure was performed using a bone putty, which was later overlaid with a collagen matrix membrane (brand name "Neomem" product of Citagenix). The remaining nine patients received dental implants which were placed into an edentulous residual alveolar ridge space. All surgical sites (and jaw bone) were exposed using full thickness periodontal flaps and after the implants had been torqued into their final position (and cover screws had been placed) the silver hydrosol gel (32 ppm) was liberally applied around the implant head and underneath the periodontal flap.

After the flap had been sutured shut, more silver hydrosol gel (32 ppm) was applied on top of the incision/sutures and held in place by a cotton gauze pad for an additional 10-15 minutes. Patients were then placed on a ten day regimen of three times daily mouth rinses with silver hydrosol 10 ppm combined (mixed) with 3% aqueous hydrogen peroxide solution. This specific formulation was developed to assist in disinfection and cleansing of the wound and the surrounding tissues.

Clinical Results: These patients were all put on a post operative recall program which involved a follow up phone call by our staff at 24 and 72 hours and a scheduled recall visit at 7-10 days and then again at 21-30 days post operation. All 11 dental implant patients successfully completed the recall program and 10 out of 11 patients said that they experienced a marked decrease in both pain and swelling within the first 24-36 hours post operation. In fact, the majority of these patients also commented that they had not taken the prescription pain killers and anti-inflammatory medications we had prescribed, much beyond the first 24 hours after surgery. Three of the 11 patients were placed on a regimen of antibiotic therapy for 10 days post operation (amoxicillin 500 mg tabs, 1 tab three times daily for 10 days) and it appeared to us that all three of these patients exhibited signs and symptoms of accelerated healing—very little swelling and edema was noted by one week post operation. By 21 days post operation the incisions in the tissue (over top of the dental implants) were virtually undetectable. It appears that the antibiotic and the silver hydrosol are synergistic. From our clinical experience the above findings were highly unusual and directly attributable to the use of the silver products.

Bone Augmentation and Sinus 'Lifts': For this evaluation a total of seven patients were followed after being surgically implanted with an osteogenic bone substitute material referred to as "bone putty". Four of these seven patients received bone augmentation to repair an existing alveolar ridge defect; two patients received a bone augmentation procedure simultaneous with the placement of a dental implant, and one patient received bone augmentation as part of a sinus lift procedure simultaneous with the placement of two dental implants. In all seven patients the surgical sites (and jaw bone) were exposed using full thickness periodontal flaps, and after the bone putty had been applied and shaped to fill-in the osseous defect, a collagen matrix membrane (Neomem) was secured over the top of the bone putty and underneath the perimeter of the periodontal flap. Before the flap was sutured shut, liberal amounts of the silver hydrosol gel (32 ppm) were applied over top of the membrane and underneath the periodontal flap. After the flap was sutured shut, more silver hydrosol gel was applied on top of the incision/sutures and held in place by a cotton gauze pad for an additional 10-15 minutes. Patients were then placed on a ten day regimen of three times daily mouth rinses with silver hydrosol 10 ppm combined (mixed) with 3% aqueous hydrogen peroxide solution.

Clinical Results: All seven patients were put on a post operative recall program which involved a follow up phone call by our staff at 24 and 72 hours and a scheduled recall visit at 7-10 days and then again at 21-30 days post operation. All seven of these patients successfully completed the recall program and six out of seven patients said that they experienced a marked decrease in both pain and swelling within the first 24-36 hours post operation. More than half of this patient group commented that they had not taken the prescription pain killers and anti-inflammatory medications we had prescribed, much beyond the first 24 hours after surgery. All seven of these patients were placed on a regimen of antibiotic therapy for ten days post operation (amoxicillin 500 mg tabs, 1 tab three times daily for ten days), and once again it appeared to us that like the implant patient group these patients also exhibited signs and symptoms of accelerated healing—very little swelling and edema was noted by one week post operation and by 21 days post operation the incisions in the tissue were virtually undetectable. From our clinical experience the above results were highly unusual and directly attributable to the use of the silver products.

Periodontal Surgery: The following procedures required the elevation of either a split thickness or full thickness periodontal flap. Silver hydrosol gel (32 ppm) was then applied either underneath the periosteum (in the case of a full thickness flap) or on top of the connective tissue (in the case of a split thickness flap) prior to the flap being repositioned and sutured back into place.

Autogenous Connective Tissue Grafts: For this evaluation a total of 13 different patients underwent 17 separate tissue graft procedures to correct lack of attached gingival tissue. All 13 patients were treated using a split thickness flap into which a collagen matrix membrane (Neomem) was inserted and secured with sutures. Before these flaps were sutured shut, liberal amounts of the silver hydrosol gel (32 ppm) were applied over top of the membrane and underneath the periodontal flap. After these flaps were sutured shut, more silver gel was then applied on top of the incision/sutures and held in place by a cotton gauze pad for an additional 10-15 minutes. Patients were then placed on a ten day regimen of three times daily mouth rinses with silver hydrosol 10 ppm combined (mixed) with 3% aqueous hydrogen peroxide solution.

Clinical Results: All 13 of these patients were put on a post operative recall program which involved a follow up phone call by our staff at 24 and 72 hours and a scheduled recall visit at 7-10 days and then again at 21-30 days post operation. All 13 of these patients successfully completed the recall program and 9 out of 13 patients said that they experienced a marked decrease in both pain and swelling within the first 24-72 hours post operation. The remaining three patients experienced what would be considered as normal amounts of swelling and pain. All 13 of these patients were placed on a regimen of antibiotic therapy for ten days post operation (amoxicillin 500 mg tabs, 1 tab three times daily for ten days) but only 10 of these 13 patients completed their daily regimens of antibiotics and daily mouth rinses. It was observed that three of the four patients that experienced 'normal pain and swelling' were also amongst the group that did not complete their antibiotic therapy or mouth rinses. Amongst that group of patients which did complete their daily antibiotics and mouth rinses, it once again appeared to us that these patients exhibited signs and symptoms of accelerated healing—very little swelling and edema was noted by one week post operation and by 21 days post operation the incisions in the tissue were virtually un-detectable. From our clinical experience the above findings were highly unusual and directly attributable to the use of the silver products.

Deep Scaling and Gingival Curettage: In this experiment a total of 18 different patients had a total of 23 separate quadrants of deep scaling and gingival curettage (under local anesthesia) to help eliminate deep gingival pocketing and promote gingival tissue re-attachment. All 18 patients were treated using a non surgical technique where the tooth roots were thoroughly instrumented (utilizing a combination of ultrasonic instruments, hand scalers and Gracey curettes) and the inner layer of sulcular epithelium was intentionally scraped away. After the tissues had been thoroughly debrided, liberal amounts of the silver hydrosol gel (32 ppm) were syringed or flushed into the gingival pockets using a 412T Monoject curved tip syringe. A gauze pad soaked with silver gel was then applied (with considerable pressure) to help reposition and re-attach the tissues. Patients were then placed on a ten day regimen of three times daily mouth rinses with silver hydrosol 10 ppm combined (mixed) with 3% diluted hydrogen peroxide.

Clinical Results: All 18 of these patients were put on a post operative recall program which involved a follow up phone call by our staff at 24 and 72 hours and a scheduled recall visit at 7-10 days and then again at 21-30 days post operation. Only 12 of the original 18 patients successfully completed the recall program but all 12 of these patients said that they experienced little if any post operative discomfort and or swelling. Amongst the group of patients which did complete their daily mouth rinses, it once again appeared to us that these patients exhibited signs and symptoms of accelerated healing—very little swelling and edema were noted by one week post op and by 21 days post operation the sulcular epithelium was pink and firm and exhibited very little if any bleeding upon probing. There was also a very noticeable reduction in pocket depth amongst that patient group which continued the use of the daily mouth rinses (post operatively). Further study as to the effects of these daily mouth rinses on reduction of pocket depths post scaling and root planning is warranted given that the above findings were highly unusual, and we believe are directly attributable to the use of the silver products.

Root Amputation: In this evaluation a total of two different patients underwent the amputation of the medial buccal root of an upper first molar after root canal therapy on that tooth root had failed. Full thickness periodontal flaps were laid to expose the buccal and interproxial plates of bone covering the root tip. Bone was then removed from around the root tip which was then 'cut' away from the remainder of the tooth and pried out of its socket with an elevator. The socket was then thoroughly debrided with a curette and flushed clean using a 10 ppm solution of silver hydrosol. Before the flaps were sutured shut, liberal amounts of the silver hydrosol gel (32 ppm) were applied into the socket and underneath the periodontal flap. After these flaps were sutured shut, more silver gel was then applied on top of the incision/sutures and held in place by a cotton gauze pad for an additional 10-15 minutes. Patients were then placed on a ten day regimen of three times daily mouth rinses with silver hydrosol 10 ppm combined (mixed) with 3% aqueous hydrogen peroxide solution.

Clinical Results: Both of these patients were put on a post operative recall program which involved a follow up phone call by our staff at 24 and 72 hours and a scheduled recall visit at 7-10 days and then again at 21-30 days post operation. Both patients successfully completed the recall program and said that they experienced a marked decrease in both pain and swelling within the first 24 hours post operation. Both patients also exhibited signs and symptoms of accelerated healing—very little swelling and edema was noted by one week post operation and by 21 days post operation the incisions in the tissue were (once again) virtually un-detectable. The tissue probings into the newly created furcation were also minimal and exhibited very little bleeding. From our clinical experience the above findings were highly unusual and directly attributable to the use of the silver hydrosol products.

Apicectomy/Retrofill: This evaluation included a total of three different patients who underwent separate surgical procedures to correct failed root canal treatment on two maxillary centrals and one lateral incisor utilizing an apicectomy and retro fill procedure which involved the creation of a full thickness periodontal flap over the area of the root tips. A small window of bone was then removed and the root tip was exposed and isolated from the surrounding bone. The root tip was then beveled (cut back) and the surrounding inter-dental bone was debrided and thoroughly rinsed with a 10 ppm solution of ASAP. A small inverted cone shaped hole was then prepared in the end of the root tip (within the old root canal system of the root) which was then plugged full of zinc oxide-eugenol with polymer reinforcement (IRM brand restorative material—Dentsply International). The area was once again thoroughly rinsed with a 10 ppm solution of silver hydrosol and before the flaps were sutured shut, liberal amounts of the silver hydrosol gel (32 ppm) were applied into the surgical defect and underneath the periodontal flap. After these flaps were sutured shut, more silver gel was then applied on top of the incision/sutures and held in place by a cotton gauze pad for an additional 10-15 minutes. Patients were then placed on a ten day regimen of three times daily mouth rinses with silver hydrosol 10 ppm combined (mixed) with 3% aqueous hydrogen peroxide solution.

Clinical Results: All three of these patients were put on a post operative recall program which involved a follow up phone call by our staff at 24 and 72 hours and a scheduled recall visit at 7-10 days and then again at 21-30 days post operation. All three patients successfully completed the recall program and reported that they experienced a marked decrease in both pain and swelling within the first 24 hours post operation. These patients also exhibited signs and symptoms of accelerated healing—very little swelling and edema was noted by one week post operation and by 21 days post operation the incisions in the tissue were virtually un-detectable. From our clinical experience the above results were highly unusual and directly attributable to the use of the silver products.

Restorative Procedures: The following procedures required the cleansing and disinfecting the tooth preparation after the old restoration had been removed and prior to placement and bonding of the restorative filling.

Placement of Composite (White) Fillings: Restorative procedures were performed on 39 different teeth amongst 26 different patients. Once the old amalgam and composite fillings had been successfully removed and all visible signs of new decay had been eliminated, the tooth preparation was modified as needed. We then implemented the following protocol to help disinfect the dentine and minimize the amount of residual bacterial contamination within the dentinal tubules: The entire tooth preparation was thoroughly rinsed and scrubbed with a cotton pellet for a minute or so and then allowed to sit for a further minute, using a combined solution of silver hydrosol 10 ppm mouth rinse and 3% aqueous hydrogen peroxide solution—a formulation developed to assist in disinfection and cleansing of the tissues. The preparation was then given a final rinse with silver hydrosol 10 ppm solution and air dried. The rinse is optional and sterile water could be substituted for silver hydrosol, but we believe leaving dried silver hydrosol on the tooth surface improves long-term sterility. Our standard protocols for the placement of a bonded composite restoration were then followed starting with acid etching of the dentine for 10-15 seconds with 38% Ortho-phosphoric Acid. Of course, the region from which the decay had been removed could be filled with any acceptable dental restorative filling material.

Clinical Results: All 26 of these patients were put on a post operative recall program which involved a follow up phone call by our staff at 24 hours and then a scheduled recall visit at 21-30 days post operation. Patient's fillings were assessed for any signs of temperature sensitivity. Although all 26 patients were successfully contacted by phone within the first two-three days post operation, only 17 of the original 26 patients successfully completed the 21 day recall program. Of those 17 patients which we were able to follow for more than 21 days post operation, NONE of them experienced any noticeable post operative temperature sensitivity whatsoever, which from our clinical experience is highly unusual and may very well be attributable to the use of the silver products. Further study of this specific product application is highly recommended, given the potential size and scope of this market and its potential clinical implications.

Crown and Bridge Procedures: The following procedures were all non-surgical in nature and required either; a) irrigation of gingival tissues with the silver hydrosol 10 ppm solution after placement and removal of gingival retraction cord or b) application of silver hydrosol gel (32 ppm) followed by use of the 10 ppm silver hydrosol mouth rinse after performing a gingivoplasty to create an "ovate pontic" or c) the cleansing and disinfecting the tooth preparation with the silver hydrosol after removal of the temporary crown prior to cementation of the permanent crown.

Gingival Retraction Cord: Irrigation of gingival tissues with the silver hydrosol after placement and removal of gingival retraction cord was carried out at 49 sites on 28 different patients. Gingival retraction cord was packed into the gingival sulcus to help expose the crown margin in order to obtain an accurate final impression. After the retraction cord was removed from around the neck of the tooth, a temporary crown was then fabricated and cemented. Typically this caused some minor amounts of bleeding and irritation and so after the retraction cord was removed, liberal amounts of the silver hydrosol gel (32 ppm) was applied around and into the gingival sulcus using a 412T Monoject curved tip syringe. After the bleeding had stopped, more silver gel was then applied around the temporary crowns and held in place by a cotton gauze pad for an additional 3-5 minutes. Patients were then placed on a ten day regimen of three times daily mouth rinses with silver hydrosol 10 ppm combined (mixed) with 3% aqueous hydrogen peroxide solution to promote cleaning of the wound and surrounding tissues.

Clinical Results: This entire patient group was put on a post operative recall program which involved a follow up phone call by our staff at 24 and 72 hours. Minimal amounts of discomfort were noted in these follow up appointments. Since this patient group was already scheduled two weeks later for the insertion of their crowns, the health and integrity of the gingival tissues was clinically assessed at this time. In all but three of these patients, by two weeks post operation, the gingival tissues had completely healed and appeared pink and firm (healthy) and exhibited very little, if any, bleeding. From our clinical experience the above findings were highly unusual and appear to be attributable to the use of the silver products.

Cleaning & Disinfection Following Removal of Temporary Crowns: in this evaluation 49 teeth on 28 different patients were treated in the following manner. At the crown insertion/cementation appointment and after the temporary crowns had been removed, the excess temporary cement was removed. The tooth preparations were then scrubbed clean using a cotton pellet soaked in silver hydrosol 10 ppm mouth rinse which included a mixture with 3% aqueous hydrogen peroxide solution. The disinfected surface was given an optional rinse (sterile water or silver hydrosol) and air dried prior to application of the permanent crown.

Clinical Results: This entire patient group was placed onto a limited post operative recall program which involved a follow up phone call by our staff at 24 and 72 hours and a scheduled recall visit at 7-10 days IF the patient was experiencing any sort of post operative discomfort and or sensitivity. Only two out of 28 patients were seen for post operative. follow ups, complaining of sensitivity on biting. As far as we could determine, the use of the silver hydrosol to cleanse and disinfect the tooth preparation(s) worked exceedingly well to a) reduce the incidence of post operative temperature sensitivity and b) to aid in the thorough decontamination and cleansing of the tooth preparation. From our clinical experience the above findings were unusual and attributable to the use of the silver products. We believe that further investigation into the effects of this silver hydrosol on both decreased post operation sensitivity and increased bond strengths should be studied further.

Gingivoplasty for creation of Ovate Pontics: Eight different patients had gingivoplasties (tissue re-contouring) performed on eight edentulous sites adjacent to fixed bridge abutments. This tissue recontouring was done to create a concave elliptical shaped depression in the tissue to receive what is called an ovate pontic which gives the cosmetically more acceptable appearance that the pontic tooth is emerging from the gum rather than just laying on top of it). The depression in the tissue was created with a football shaped high speed diamond drill bit. Immediately after the gingivoplasty is performed the tissue looks like raw exposed, bleeding skin. Liberal amounts of the silver hydrosol gel (32 ppm) were then applied on top of the exposed tissue and held in place by a cotton gauze pad for an additional 3-5 minutes. After a temporary bridge had been fabricated to hold the shape of the ovate depression, more silver gel was applied underneath the temporary bridge now cemented into place. Patients were then placed on a ten day regimen of three times daily mouth rinses with silver hydrosol 10 ppm combined (mixed) with 3% aqueous hydrogen peroxide solution.

Clinical Results: This entire patient group was put on a post operative recall program which involved a follow up phone call by our staff at 24 and 72 hours. Minimal amounts of discomfort were noted in these follow up appointments. Since this patient group was already scheduled two weeks later for the insertion of their final bridgework, the health and integrity of the gingival tissues were clinically assessed at this time. In all eight of these patients, by two weeks post operation, the ovate depressions in the edentulous ridge had completely healed and appeared pink and firm (healthy). Since the tissue had all re-epithelialized there were no clinical signs of bleeding. From our clinical experience the above findings were highly unusual and appear to be attributable to the use of the silver hydrosol products.

Removable Prosthetics (Dentures): The following procedures were all non-surgical in nature and required either the application of silver hydrosol gel (32 ppm) to the under side of the denture and/or the use of a daily 10 ppm silver hydrosol mouth rinse.

Cleansing and Disinfection of Dentures: For this evaluation 24 Dentures (14 partial and 10 complete) from 24 different patients were treated with silver hydrosol gel (32 ppm) to cleanse and disinfect the denture acrylic and to help eliminate denture odor. The acrylic portions of these dentures were scrubbed thoroughly with the silver gel. The dentures were then soaked for 10 minutes in a 10 ppm silver hydrosol solution which was combined (mixed) with 3% aqueous hydrogen peroxide solution. The dentures were then rinsed and dried thoroughly. A small amount of silver hydrosol gel (32 ppm) was then applied to the underside of these dentures before they were inserted into the patients' mouths. Patients were then given a small amount of silver gel to take home and apply daily (for ten days) to the underside of their dentures.

Clinical Results: This entire patient group was put on a post operative recall program which involved a follow up phone call by our staff at 24 and 72 hours. A vast majority—23 out of 24—patients noticed an almost immediate and substantial reduction in the 'smell' of their dentures. Only 15 of the 24 denture patients returned for their one week recall, but all 15 of these patients (and our staff) noticed a dramatic reduction in the smell and odor once emanating from the dentures. The issue of 'smelly dentures' is clearly related to excessive bacterial growth over time and so it is our clinical experience that the above findings were highly unusual and appear to be directly attributable to the use of the silver products.

Treatment of Denture Stomatitis/Sore Mouth: For this evaluation seven different patients suffering from denture stomatitis/sore mouth were treated using the 10 ppm silver hydrosol mouth rinse. First, the denture was cleaned and disinfected by soaking it in a solution of 10 ppm silver hydrosol combined (mixed) with 3% aqueous hydrogen peroxide solution. A small amount of silver hydrosol gel (32 ppm) was then applied to the underside of these dentures before they were inserted into the patients' mouths, and the patients were then given a small amount of silver gel to take home and apply daily (for ten days) to the undersides of their dentures.

Clinical Results: This entire patient group was put on a post operative recall program which involved a follow up phone call by our staff at 24 and 72 hours. Minimal amounts of discomfort were noted during these first two follow up calls. By the week one recall visit ALL seven patients had noticed a distinct improvement in the fit and comfort of their dentures. Clinically, the initial redness and puffiness that was present underneath their dentures had almost completely resolved in all but one patient. For this patient we added a three time daily regimen of silver hydrosol mouth rinse and within the week this patient's redness and discomfort had also subsided. It is our clinical experience that the above findings were highly unusual and appear to be directly attributable to the use of the silver products.

Additional Silver Hydrosol Applications: In performing the above tests of the invention additional uses of the material and the inventive methods became apparent. These applications fall into two categories. Either the silver hydrogel can be used as a disinfectant rinse or surface disinfectant as explained above. Or the silver hydrogel can be added to an already existing product to confer antimicrobial properties to a variety of products. In some cases the silver hydrosol is simply added to the products in place of water. That is, the silver hydrogel is used to hydrate the product. In other cases, it will be apparent to one of ordinary skill in the art that the product in question is not compatible with water. In that case it is already known (see WO 2006/074117) that the metallic silver nanoparticles in silver hydrosol can be collected by (for example) centrifugation, filtration or evaporation of the suspending water and the resulting powder added directly to other compositions (either as a neat powder or suspended in a solvent compatible with the product in question). In the following discussion the material will be referred to as "silver hydrosol" but those of ordinary skill in the art will recognize that where the combination must be anhydrous, silver particles prepared from silver hydrosol will actually be use.

In keeping with the disclosed inventive methods silver hydrosol solution or gel solution can be applied either directly into or around a surgical site (post operatively) using a syringe to help flush out and cleanse the affected tissue. The formation of post operative "dry sockets", impacted food debris, infection and sequestrum of bone can all cause inflammation, pain and delayed healing. The application of the silver hydrosol solution to the affected area can help to rapidly reduce/eliminate these symptoms.

The silver hydrosol plus dilute hydrogen peroxide solution can be readily used as a Periodontal Irrigant & Oral rinse for treating oral conditions such as halitosis, periodontal disease and even xerostomia. This solution can be utilized in a number of different ways: a) it can be swished around inside the mouth and then spat out or b) it can be applied to the tissues using a syringe or c) it can be used as a periodontal irrigant in combination with ultrasonic cavitation. The chemistry of this solution has both a therapeutic and a germicidal effect. After completing sub-gingival irrigation with his solution using a fine tipped syringe (loaded with the above mentioned solution) one can syringe a thicker layer of silver hydrosol gel to cover these same infected tissues—the viscous silver hydrosol gel takes time to dissipate, thus providing additional contact time with concomitant greater antibacterial persistence and therapeutic effect. The goal of adding utilizing daily use of an oral solution of the silver hydrosol is to provide a continuous dynamic antimicrobial bacteriostatic environment capable of reducing bacterial bio-burden as well as post operative infection and inflammation thereby resulting in an increased rate of wound healing.

An IV (intravenous solution) Bag containing an antimicrobial solution of either sterile normal saline and silver hydrosol or sterile lactated Ringers solution and silver hydrosol is a useful way to deliver an antimicrobial/wound healing solution. The delivery of an antimicrobial saline solution (from the IV Bag) to any number of surgical sites by either flushing or rinsing using either a manual syringe or a mechanical device such as a hand-piece with built-in irrigation tubing has the ability to reduce the bacterial bio-burden and the risk of contamination of the surgical site as well as reduce the incidence of post operative inflammation and infection. The IV Bag is a convenient way to deliver the IV solution for the user. Suspending the bag can provide gravity assisted delivery of the solution (alternatively, a peristaltic pump can be used to pressurize the delivery) to the patient.

Gel Foam is an existing dental material composed of absorbable substances and is intended to be 'packed' into fresh extraction sockets to stop bleeding. According to the methods of the invention, Gel Foam can be readily impregnated with silver hydrosol or the hydrosol can be expressed directly into the socket either prior to or after the placement of Gel Foam. By adding the silver hydrosol to the Gel Foam product can now provide a continuous dynamic antimicrobial bacteriostatic environment capable of reducing bacterial bio-burden as well as post operative infection and inflammation, thereby resulting in an increased rate of wound healing.

Alternatively, materials such as Hemostyp (a branded commercially available Absorbable Cellulose Sponge product) can also be impregnated with the electrolytic silver hydrosol. Products like Hemostyp are typically used to help stop bleeding (after a tooth extraction) by placing the cellulose sponge into the fresh extraction socket. By adding the silver hydrosol to the Hemostyp product (or similar products), the product can now provide a continuous dynamic antimicrobial bacteriostatic environment capable of reducing bacterial bio-burden as well as post operative infection and inflammation which results in an increased rate of wound healing.

Currently, periodontal wafer chips which contain antimicrobial substances such as tetracycline or chlorhexidine are on the market. These pharmaceutical drugs are impregnated into the absorbable wafer and are then placed into specific localized areas of the gingival tissues (where there is either deep pocketing and or active bacterial infection). Over time, this absorbable matrix breaks down, the wafer is absorbed by the body and the drug is released within the tissues and has its localized effect. Silver hydrosol could be impregnated into a small resorbable gelatinous wafer/matrix or absorbable cellulose matrix which is designed to 'leach' or deposit the silver hydrosol antimicrobial agent at a steady rate over time into the surrounding local tissues. Impregnating a small absorbable wafer with electrolytic silver hydrosol allows it to be placed into specific localized areas of the gingival tissues where there is either deep pocketing and or active bacterial infection. Over time, this absorbable matrix breaks down and is absorbed by the body. According to the methods of the present invention, a new and innovative electrolytic silver hydrosol can now be utilized as part of a localized delivery system. By adding silver hydrosol to this wafer/matrix, the product can now provide a continuous dynamic antimicrobial bacteriostatic environment capable of reducing bacterial bio-burden as well as post operative infection and inflammation. Because the silver hydrosol solution is not metabolized by the body, it has no undue effects on human tissue and, therefore, is not in any way toxic to the bodies organ systems such as the liver and or the kidneys as are so many of the other antimicrobial agents. Furthermore, combining the use of this antimicrobial wafer with the systemic use of antibiotics, a potentiating or synergistic effect can also be achieved. These new applications of a periodontal wafer/matrix product result from the combination with electrolytic silver hydrosol.

Introduction to Bone Graft Materials and Types:

Autogenous Bone Grafts. Also called auto-grafts, these types of grafts are made from the patient's own bone, harvested from elsewhere in the body. Typical harvest sites include the chin, jaw, bone of the lower leg (tibia), hip (iliac crest) or the skull (cranium). The autogenous bone graft has traditionally been considered the "gold standard" as a graft material because it is "live bone" complete with the living cellular elements that enhance bone growth. These include osteogenesis (bone formation from cells), osteoconduction (bone formation via migration upon a scaffold) and osteoinduction (bone formation by proteins such as BMP [bone morphogenetic proteins], which direct cells to form new bone).

A potential downside of autogenous bone grafting, however, is that it involves a second procedure to harvest the bone, which may be painful and not in some patients' best interest, depending on their condition. It also may not be a viable option in instances where the patient's overall bone quality and/or density is poor, or when a large volume of graft material is required.

Allogenic Bone. Allogenic bone, also called allograft, is bone derived from a genetically unrelated member of the same species. It's typically non-vital (dead) bone harvested from a cadaver, then processed using a freeze-drying method to extract all the water. Allogenic bone cannot produce new bone on its own because it's neither osteogenic (like autograft) nor osteoinductive (like BMP). Rather, its primary mechanism of action is that it is osteoconductive, and it serves as a framework or scaffold over which bone from the surrounding bony walls can grow to fill the defect or void.

Xenogenic Bone. Similar to allogenic bone, xenogenic bone is non-vital bone, but it is derived from a different species, usually bovine. Because the potential for immune rejection and contamination by viral proteins is higher in bovine bone than in human cadaver bone, xenograft material is processed at very high temperatures (600-1,000° C.). A xenograft's mechanism of action is similar to that of allograft, and it serves as an osteoconductive framework on which bone from the surrounding area can grow to fill the void.

Allogenic and Xenogenic grafting options are preferred by many patients and dental professionals alike because they eliminate the potentially painful second harvesting procedure. However, because allograft and xenograft lack autograft's bone forming properties, bone regeneration may take somewhat longer than it does when using the patient's own bone, and the outcome may be less predictable.

Bone Graft Substitutes. Bone graft substitutes are commercially produced synthetic materials that have many of the same bone forming properties as human bone, and are a safe and proven alternative to both auto-graft and allograft. One of the advantages of using a bone graft substitute instead of autogenous bone is that it eliminates the need to harvest the patient's own bone, thus potentially reducing the risk and pain associated with the harvest procedure. Bone graft substitutes include Demineralized Bone Matrix/Demineralized Freeze-Dried Bone, Ceramics, Graft Composites and Bone Morphogenesis Proteins.

Demineralized Bone Matrix (DBM)/Demineralized Freeze-Dried Bone Allograft (DFDBA). DBM/DFDBA is specially processed allograft bone; DBM/DFDBA contains collagen, proteins and growth factors that are extracted from the allograft bone. It is available in the form of a powder, crushed granules, putty, chips or as a gel that can be injected through a syringe.

Ceramics. Ceramics are also used as a substitute for bone grafts, and are available in many forms such as porous and mesh. Although ceramics may provide a framework for bone growth, they contain none of the natural proteins that influence bone growth and may be associated with inflammation in some patients.

Graft Composites. Graft composites use combinations of other bone grafting materials and/or bone growth factors to gain the benefits of a variety of different substances. Typical combinations in use today include: a collagen/ceramic composite, which closely reproduces the composition of natural bone; DBM combined with bone marrow cells, which aid in the growth of new bone and a collagen/ceramic/auto-graft composite.

Bone Morphogenetic Proteins. Bone morphogenetic proteins (BMPs) are proteins naturally produced in the body that regulate bone formation and healing. A commercially available BMP is INFUSE Bone Graft (rhBMP-2/ACS).

Dental Bony Defects. Examples of dental bony defects include: (i) Pneumatized Sinus and Augmentation of the Maxillary Sinus Floor ("Sinus Lift"); (ii) Peri-implant Bony defects around integrated dental implants; (iii) Infra and intra bony periodontal defects; (iv) Alveolar Ridge Augmentation; and (v) Fresh Extraction Socket(s). These defects can be ameliorated with the appropriate bone material.

Approximately 20 BMPs with different amino acid sequences have been isolated to date, but only six appear capable of actually initiating bone growth. Of these, BMP-2 has demonstrated the greatest potential to form bone. To produce a practical version of BMP, scientists isolated one protein (BMP-2) from the bone tissue and used recombinant DNA technology to create genetically engineered cells to produce recombinant human BMP-2 (rhBMP-2). It was determined that these cells could produce pure, natural human BMP-2 protein, a substance capable of initiating bone growth. Recombinant human Bone Morphogenetic Protein-2 (rhBMP-2) has already been studied for safety and efficacy in inducing adequate bone in patients with all of the aforementioned bony defects and the results were very positive.

All of the above mentioned bony defects can (according to the methods of the present invention) now be advantageously utilized in combination with electrolytic silver hydrosol by impregnating the absorbable collagen sponge (ACS) with the silver hydrosol (specifically by soaking the collagen sponge in a sterile solution of silver hydrosol (and RhBMP-2) prior to its application in the mouth. Electrolytic silver is non-toxic to human tissue and highly effective against a broad spectrum of both Gram positive and Gram negative bacteria, viruses, yeast and fungi and has been proven to provide a continuous dynamic antimicrobial bacteriostatic environment capable of reducing bacterial bio-burden and thus post operative infection, inflammation and pain. It has also been established as a powerful wound healing agent capable of significantly accelerating the healing process. No bacteria or virus has ever been shown to develop a resistance to silver hydrosol.

The Need for Antimicrobial RhBMP/ACS Products. As with any surgery, surgical treatment to promote bone growth in the jaw is not without risk. A variety of complications related to surgery or the use of rhBMP-2/ACS may occur, either alone or in combination. Some of these may be severe and affect overall outcome. Additional surgery also may be required to correct these complications. Possible complications include: 1) Infection—a major justification for the addition silver hydrosol as an antimicrobial agent; 2) inflammation—also managed by the addition of silver hydrosol; 3) Itching; 4) Pain—also ameliorated by silver hydrosol; 5) Allergic reaction; 6) Edema (swelling)—also controlled by addition of silver hydrosol; 7) Erythematous tissue; 8) Hematoma; 9) Incisional complications; 10) Scar formation—also responsive to addition of silver hydrosol; and 11) Tissue or nerve damage—again ameliorated by addition of silver hydrosol.

Application Method. RhBMP-2 Bone Graft material is packaged with a collagen sponge and sterile water for reconstitution. This water can be replaced with silver hydrosol. Prior to surgery, the powdered rhBMP-2 is mixed with the silver hydrosol to create a liquid solution. The sponge is soaked in the antimicrobial silver rhBMP-2 protein solution for at least 15 min. For dental application the product is then applied to the surgical site.

Transplantation and/or Reimplantation. Human dental Follicle cells (HDFCs) can be impregnated with and/or soaked in electrolytic silver hydrosol (according to the present invention) prior to surgical transplantation or reimplantation. The Dental Follicle (DF) surrounding the developing tooth germ is an ectomesenchymal tissue comprised of various cell populations derived from the cranial neural crest. DF cells are believed to contain precursor cells for cementoblasts, periodontal ligament cells and odontoblasts ("dental tissues"). Bone Morphogenic Proteins (BMPs) produced by Hertwigs epithelial root sheath or present in enamel matrix derivatives (EMD) appear to be involved in the control of Dental Follicle Cell differentiation If HDFC can be stimulated by rhBMP-2 then it appears that rh-BMP-2 may play a central role in the intra-oral (in vivo) transplantation and or reimplantation of HDFCs and their subsequent differentiation and growth into a variety dental tissues. It is believed that by soaking the HDFCs and or rhBMP-2 in a solution of electrolytic silver hydrosol solution prior to the intra-oral reimplantation of these same products, a continuous dynamic antimicrobial bacteriostatic environment can be created, capable of reducing bacterial bio-burden and thus the risk of post operative infection and inflammation. The ultimate result is a higher rate of success of transplantation and differentiation of these dental tissues utilizing the electrolytic silver hydrosol.

A variety of permanent dental cements can be impregnated with silver hydrosol including epoxy resin cements, glass ionomer and resin modified glass ionomer cements (which are used to permanently cement crowns and bridgework).

Such cements also include those which are either auto-cured, light cured or dual cured (those using a combination of light activation and chemical reaction to set the cement). Any number of commonly used permanent dental cements such as zinc phosphate and zinc polycarboxylate cements can also be readily combined with the silver hydrosol solution. By adding the silver hydrosol to these cements, one is able to provide a continuous dynamic antimicrobial bacteriostatic environment capable of reducing bacterial bio-burden and thus post operative inflammation, infection and sensitivity which are particularly important with vital teeth.

A variety of temporary cements (both eugenol and non-eugenol based) can readily be impregnated with silver hydrosol so that inflammation and infection are reduced in the area of temporary restorations and other locations where these cements are employed.

Temporary or intermediate restorative materials (without eugenol) composed of auto-cured resin modified glass ionomer, fluoride and white cupric or copper oxide can also be impregnated with silver hydrosol. By adding the silver hydrosol to this type of intermediate restorative material, we are able to provide a continuous dynamic antimicrobial bacteriostatic environment capable of reducing bacterial bio-burden and thus post operative inflammation, infection and sensitivity (which are especially important with vital teeth). Such antimicrobial cements have the ability to arrest and stop bacterial infection in human teeth and promote remineralization of subjacent infected dentine plus initiate the sclerotic closure of the dentinal tubule complex. This in turn reduces/eliminates the patient from feeling hypersensitivity due to cold or air stimulation.

Light cured flowable composite resin materials which are composed of methacrylic esters and inorganic fillers (such as those manufactured for Patterson Dental) can be made to function as an antimicrobial product by the addition of silver hydrosol. The silver hydrosol can be released (at a steady rate over time) from the resin composite matrix thereby providing a continuous dynamic antimicrobial bacteriostatic environment capable of reducing bacterial bio-burden which results in less cariogenic activity and a lower incidence of tooth decay.

Methyl and ethyl methacrylate acrylics (used for making temporary acrylic restorations, partial crowns, crowns and bridgework) can also be impregnated with silver hydrosol. By adding the silver hydrosol to these products, we are able to provide a continuous dynamic antimicrobial bacteriostatic environment capable of reducing bacterial bio-burden and thus a lower incidence of post operative infection, less inflammation in the surrounding gingival tissues and less odor from the temporary acrylic material.

The silver hydrosol antimicrobial gel can be impregnated (i.e., mixed into or applied to) into a number of disposable dental products such as retraction cord, acrylic monomer and polymer material utilized in the fabrication of partial denture acrylic saddles, etc. By adding the silver hydrosol to these products, the goal is to provide a continuous dynamic antimicrobial bacteriostatic environment capable of reducing bacterial bio-burden and thus post operative infection and inflammation. Alternatively, these same materials may also be soaked in a solution of silver hydrosol prior to use.

Silver hydrosol material can also be utilized as an antimicrobial additive in a variety of denture cleansing products (such as foams, gels, dissolving tablets and or liquid solutions).

Silver hydrosol in either a liquid solution or a gel format can be used as an antimicrobial additive in a variety of soft denture reline materials (in either lab processed or chair-side reline products). The silver hydrosol solutions can also be utilized as an antimicrobial additive to denture base soft tissue conditioners (typically used for therapeutic treatment of irritated soft tissues under denture base materials (due mostly to bacterial and or fungal infections such as *Candida albicans*). The silver hydrosol solution can also be used to treat odor causing bacteria and fungi associated with old or 'dirty' dentures. Additionally, the silver hydrosol gel can be applied daily (topically) to the affected tissue underneath the denture and the patient can be put on a regimen of daily oral rinses utilizing a solution of 10% silver hydrosol with or without the addition of dilute hydrogen peroxide.

In higher concentrations (20-50% or more) the silver hydrosol solution can be used as a surface disinfectant (short acting within 10-30 minutes) and or cold liquid sterilant (long acting requiring 10 or more hours). As a disinfectant solution the silver hydrosol solution (with or without the addition of dilute hydrogen peroxide) can be used for a variety of applications:

a). soaking and disinfecting autogenous bone fragments (a.k.a. collected bone debris or "CBD") harvested during the creation of an osteotomy site for a dental implant
b). disinfection of non-porous surfaces and medical/dental Instruments (both disposables and non disposables).
c). disinfection of dental impression materials that may contain potentially infectious blood/bodily fluids.

For items a).-c). above the protocol for disinfection is normally spray, wipe, spray again and let stand for anywhere from 3-30 minutes.

Dental unit water lines can be readily disinfected by flushing the lines with a solution of silver hydrosol either with or without dilute peroxide. As a cold sterilant solution the silver hydrosol either with or without dilute peroxide can be used to soak medical/dental instruments which should be completely immersed in the solution continuously for at least 10 hours.

Resorbable/absorbable and non-resorbable suture materials can be impregnated, hydrated and or coated with silver hydrosol to create a suture material which has the benefit of antimicrobial activity/persistence without the application or use of an organic drug (but rather, the use of a disinfectant metal). By adding the specific inventive formulation of silver hydrosol to these products, one provides a continuous dynamic antimicrobial bacteriostatic environment capable of reducing bacterial bio-burden and thus post operative infection and inflammation thus reducing healing time and post operative discomfort.

Antimicrobial Toothpaste using silver hydrosol with or without dilute hydrogen peroxide and with or without bleaching agent is advantageous. Antimicrobial toothpastes (e.g., AquaFresh brand) are fairly commonplace in today's marketplace; however their antimicrobial performance is typically due to the addition of fluoride. The toothpaste according to the present invention contains electrolytic silver hydrosol in addition to fluoride ions +/− dilute hydrogen peroxide (3-10%) +/− a bleaching agent such as dilute Carbamide Peroxide (5-25%). This composition has greatly enhanced antimicrobial properties.

Antimicrobial Dental Floss (waxed). Persistent Antimicrobial activity can be imparted to Dental floss by impregnating the waxed layer of the dental floss with a solution of electrolytic silver hydrosol. The added benefit of such a product is to help effectively reduce the bacterial bio-burden in those areas where the floss makes contact with the gingival tissues.

Surgical cyanoacrylate cements or adhesives (such as Periacryl brand) can be impregnated with silver hydrosol to provide persistent antimicrobial activity during normal wound healing. Adding silver hydrosol to cyanoacrylate creates a new product able to provide a continuous dynamic antimicrobial bacteriostatic environment capable of reducing bacterial bio-burden over time and thus the risk of post operative infection and inflammation.

Products such as Emdogain (brand of enamel matrix derivative manufactured by the Straumann Company.) were designed for topical application to a suitable root surface for selective periodontal cell migration and attachment which reestablishes lost tooth supporting tissues. Adding silver hydrosol to this type of product provides a continuous dynamic antimicrobial bacteriostatic environment capable of reducing bacterial bio-burden and thus post operative infection and inflammation. Emdogain re-attachment surgery is undertaken by employing a full thickness periosteal flap to expose the osseous tissue. After the root surfaces have been treated with either EDTA or citric or phosphoric acid they should be rinsed thoroughly with a sterile saline solution containing silver hydrosol so that any contamination with either blood and or saliva (after the final rinse) is minimized due to the antimicrobial activity of the silver containing saline solution. Subsequent to the formation of new attachment, alveolar bone can also be regenerated due to osteogenic capacity of the restored periodontal ligament. Because this process of reattachment is part of normal wound healing, the addition of silver hydrosol can help reduce post operation inflammation and the risk of infection thus increasing the likelihood of successful reattachment. Patients that undergo this reattachment surgery should be advised to rinse daily with an antiseptic mouth rinse containing silver hydrosol and dilute hydrogen peroxide for three to six weeks following the procedure. Antibiotics may also be used systemically (in conjunction with the silver hydrosol rinse) to create a potentiating effect such as the one discussed above.

Silver hydrosol is also useful in rehydrating a number of materials used in dental practice. For example, resorbable collagen membranes or "collagen tapes" such as "Neo-Mem" (manufactured by Collagen Matrix, Inc., Franklin Lakes, N.J.) are provided dry and must be rehydrated before use. These membranes are non-friable membrane matrices engineered from purified type 1 collagen fibers derived from either human cadaver and or animal sources (such as bovine Achilles tendon). Intended applications for collagen membranes include use in dental surgery procedures as a material for placement in the area of a dental implant, periodontal bone defect or ridge reconstruction (using bone augmentation materials underneath the antimicrobial collagen membrane) to aid in wound healing post dental surgery. By rehydrating these products with silver hydrosol one is able to provide a continuous dynamic antimicrobial bacteriostatic environment capable of reducing bacterial bio-burden and thus post operative infection and inflammation. The silver hydrosol gel can also be applied over top of the collagen membrane after it has been positioned into the surgical site prior to and after the repositioning and closure of the mucoperiosteal flap.

Similarly, silver hydrogel can be used to rehydrate other reconstructive materials such as Alloderm Regenerative Tissue Matrix. Rehydration is accomplished by fully submersing the membrane for between two and 40 minutes depending on the thickness of the material in either a warm solution of sterile normal saline plus silver hydrosol or a solution of silver hydrosol plus sterile lactated Ringers solution. The membrane should be gently agitated in the solution to help remove any excess cryoprotectant from the membrane. When Alloderm is fully rehydrated it is soft and pliable, which allows the Alloderm to be readily aseptically trimmed to required dimensions at which stage, it is ready for application to the surgical site. Rehydration with this antimicrobial solution helps prevent a localized inflammatory tissue response to the Alloderm material as well as reduce the risk of post procedure infection. Antimicrobial persistence of the membrane once placed in its surgical site can be augmented by application of the silver hydrosol gel. By adding the silver hydrosol to these products, one provides a continuous dynamic antimicrobial bacteriostatic environment capable of reducing bacterial bio-burden and thus post operative infection and inflammation.

Other materials that can benefit from the addition or application of silver hydrosol are disposable germicidal cloths which contain one or more traditional chemical germicides. These disposable "moisture laden" germicidal cloths are intended for use in hospitals and other critical care areas (including dental and medical offices) where the control of the hazards of cross-contamination are required. These antimicrobial germicidal cloths can be used to disinfect and wipe clean surfaces and equipment such as stainless steel, Formica, glass tables, carts, baskets, counters, cabinets, telephones and other non-porous surfaces. These cloths are either non-woven (such as EcoLab's Huntington brand Asepti-Wipe II) or woven cloths and can be readily impregnated with a solution of silver hydrosol either with or without dilute hydrogen peroxide to enhance their overall disinfectant properties.

Other germicidal products such as the Citricidal brand disinfectant (manufactured by Therawerx, Ashville, N.C.) as a disinfectant wipe (either as a foaming cleanser, wipe and or sponge) can even be used to clean and wipe down the skin. The Citricidal brand disinfectant solution contains 60% active ingredients (quaternary compound from grapefruit bioflavonoids) and 40% Vegetable Glycerin USP. Citricidal is an amber-colored liquid with a mild citrus aroma. It is non-toxic, biodegradable, non-corrosive, yet highly potent. According to studies, the activity of the active ingredient of Citricidal grapefruit seed extract appears to attack the cytoplasmic membrane of the microorganisms. The active ingredients of the extract disorganize the cytoplasmic membrane, thereby preventing the uptake of amino acids. At the same time, there is a leakage of low molecular weight cellular contents through the cytoplasmic membrane thereby inactivating the pathogen. Microorganisms do not build up resistance to grapefruit seed extract ("GSE"). What is not understood is how GSE can affect the cell membranes of such a diverse group of microbes with virtually no toxicity toward animal life. Addition of electrolytic silver hydrosol to the Citricidal brand skin disinfectant (at concentration ranging from 10 ppm-32 ppm) can provide increased performance against a wide range of pathogens which results in decreased inflammation and accelerated wound healing.

The list of dental materials that can be fortified with silver hydrosol is extensive. For instance, alginate impression powders can be mixed with water that contains silver hydrosol to create an impression material that has antimicrobial activity. Such a product has antibacterial persistence and the ability to reduce the bacterial bio-burden in the stone model from which the impression is poured. The use of silver hydrosol in this application helps aid in the reduction of cross-contamination from bio-organisms such as bacteria, yeasts, other fungi and viruses.

A similar example is Reversible and Irreversible Hydrocolloid Impression materials/powder mixed with water that contains silver hydrosol to create an impression material that has antimicrobial activity. Such products will have antibacterial persistence and the ability to reduce the bacterial bio-burden in the stone model from which the impression is poured. Again, the use of silver hydrosol in this application helps aid in the reduction of cross-contamination from bio-organisms such as bacteria, yeasts, other fungi and viruses.

Germicidal Masks. Dental personnel commonly wear surgical masks both to avoid transmission of microorganisms to patients and to avoid being infected by microorganisms from patients. Most surgical masks work on a barrier filtration principle and intercept airborne microorganisms as wells as droplets containing microorganisms. However, the internal filtration media of the mask (which traps these microorganisms), typically, is not bactericidal which creates two potential problems: 1) it allows for the iatrogenic and or nosocomial spread of infections associated with the microorganisms trapped within the surgical mask and 2) these masks may become contaminated and spread microorganisms when they are subsequently handled and disposed of.

Silver hydrosol is effective for surface sterilization and might serve to ensure disinfection of surgical masks. Because surgical masks are generally not used wet, it was necessary to demonstrate that silver hydrosol dried onto surgical mask material would maintain its antimicrobial potency. Many surgical masks contain a layer of melt blown material as the filtration and absorptive portion of the mask. For the test sterile melt blown material from surgical masks was cut into discs sized to fit within standard Petri dishes. Each test disc was placed in a sterile Petri dish and covered with silver hydrosol (32 ppm silver). After soaking briefly, the material was removed and allowed to air dry under sterile conditions. Control discs were not soaked in silver hydrosol.

Test bacterial cultures of *Escherichia coli* B and *Staphylococcus aureus* were grown overnight in Nutrient Broth (Beef extract 3 g/L and Peptone 5 g/L in distilled water). The test cultures contained over 1,000,000 colony forming units (cfu) per µL. Sterile Nutrient Agar Petri plates (Nutrient Broth plus 1.5 g/L) were prepared using standard laboratory methods. Finally, 10 fold serial dilutions (using Nutrient Broth) were made of each test culture and spotted onto a disc (2 µL per spot) on the surface of Nutrient Agar within a Petri dish. Each disc was spotted with straight test culture, culture ×10-1, culture ×10-2, culture ×10-3, culture ×10-4 and culture ×1-5. Thus the spots ranged from over 2,000,000 cfu to over 20 cfu. The Petri dishes were incubated overnight in a 37° C. incubator.

Every spot on the control disc (not treated with silver hydrosol) showed strong bacterial growth. On the silver treated disc none of the serial dilutions showed growth although slight growth was seen on the area spotted with undiluted test culture. Incubation was continued for an additional 24 hr at which time the undiluted test culture spot became opaque with bacterial cells. None of the other spots showed any growth. Thus, treatment of the mask material with silver hydrosol was able to kill or inhibit at least 200,000 cfu. This is vastly higher than the concentration of microorganisms that a surgical mask is ever likely to encounter.

Thus, treatment of the mask's internal filtration material with silver hydrosol was able to kill or inhibit at least 200,000 cfu. This is vastly higher than the concentration of microorganisms that a surgical mask is ever likely to encounter. A number of areas in the practice of medicine would greatly benefit from the enhanced protection silver impregnated masks would provide, as would any endeavor which required that the workers be protected from the intentional (or unintentional) release of pathogenic organisms. It is also apparent to us that the application of silver to a wide variety of air handling filters, such as in planes, buildings, etc, would also be of great benefit.

Antimicrobial Gloves. All types of either latex, vinyl and/or co-polymer nitrile examination and surgical gloves (which have been powdered with either absorbable corn starch or oat starch during the manufacturing process) can also be impregnated with silver hydrosol by applying the silver solution onto the powder as part of a surface treatment. This can be achieved by adding the silver hydrosol solution into either the vat of liquid latex rubber and or the liquid slurry of powder (during the wet/dry manufacturing process). Once the glove is donned by the user, his or her sweat tends to mix with the powder, creating a thin film antimicrobial barrier on the skin which allows the glove user to combat potential dermatological problems as well as reduce the risk of cross-contamination of bodily fluids due to pin hole defects or rips and tears in the gloves which frequently appear during extended use. The use of the silver hydrosol solution on the powder can also help to reduce the risk of skin irritation and inflammation commonly associated with such ailments as Irritant Contact Dermatitis and Allergic Contact Dermatitis.

In a first embodiment of this glove invention, the silver hydrosol solution can be sprayed or applied onto the gloves donning powder as part of a surface treatment (the gloves are powdered using either absorbable corn starch or oat starch). Preferably, the donning powder is surface treated by adding the silver hydrosol solution into the vat containing the liquid slurry of donning powder (during the wet/dry manufacturing process). Once the glove is donned by the user, his or her sweat will mix with the powder, creating a thin film antimicrobial barrier on the skin which allows the glove user to combat potential dermatological problems as well as reduce the risk of cross-contamination of bodily fluids (and associated microorganisms) due to pin hole defects or rips and tears in the gloves which frequently appear during extended use. The use of the silver hydrosol solution on the powder can also help to reduce the risk of skin irritation and inflammation commonly associated with such ailments as Irritant Contact Dermatitis and Allergic Contact Dermatitis. Other antimicrobial gloves exist on the market, but, none of them utilize the silver hydrosol compound according the innovative and unique manufacturing methods of the present invention.

Still another object of some embodiments of the present invention is to prevent growth of bacteria, viruses, yeast and fungi on the hands, which become more active in a wet environment resulting from sweating during prolonged or frequent wearing of gloves—since the antimicrobial powder is able to create a thin film barrier on the skin, the antimicrobial performance of the silver hydrosol is more than capable of rapidly and sustainably reducing the overall number of colony forming units of microorganisms on the skin.

In a second embodiment of this invention both latex and non latex gloves (e.g., nitrile gloves) can be coated with an antimicrobial solution of Aloe Vera applied to the inside of the glove. This involves combining an antimicrobial solution of electrolytic silver nano particles with pure or diluted Aloe Vera [freeze dried or dehydrated] to create an antibacterial powder liquid or gel to be uniformly applied to the inner surface of disposable latex and non latex gloves. The process for applying the Silver Aloe Vera liquid is through immersing spraying/aerosolization and then applying a controlled dehydration process. The Silver Aloe Vera powdered material is applied by electrostatic application onto, or by tumbling the dry powdered material (surface treated with silver hydrosol) with or by aerosolizing the powder onto, the dry wearer contacting surface of a dry glove or by application of the powder onto the dry wearer-contacting surface of the glove from a fluidized bed or a non-fluidized bed of the dry powdered material with or without additives prior to stripping the glove from a glove former.

The method of manufacturing gloves involves treating a commercially available disposable glove to eliminate residue powders, soluble substances, and microorganisms, turning the glove inside out, dipping it into a solution of silver hydrosol and Aloe Vera and then heating the glove to cause water to evaporate leaving a dried layer of Aloe Vera and silver hydrosol adhered to the glove. A glove is preferably first treated with a chlorine solution or chlorine gas. Chlorine solution can help to sterilize the gloves, to wash off powders, and most importantly for natural latex gloves, to dissolve residual proteins that could potentially trigger severe allergic reactions among repeat users. After the outside surface of the glove is treated with the chlorine solution, it is turned inside out, and the glove is again treated with the chlorine solution. The residue chlorine is neutralized by using ammonia and the gloves are then dried.

An antimicrobial solution of Aloe Vera is then be prepared as follows: A concentrated solution of Aloe Vera gel is dissolved in distilled water containing between 20-32 ppm silver hydrosol to create an antimicrobial solution of Aloe Vera. The preferred concentration of Aloe Vera in solution is about 20%. To associate the silver containing Aloe Vera with the surface of the glove, the antimicrobial Aloe Vera solution can be sprayed onto the surface of the glove. Alternatively, the glove can be immersed into a solution containing Aloe Vera and silver hydrosol. The latter method is preferred because it creates a complete and even distribution of the silver Aloe Vera solution.

In one preferred embodiment, the dipping process is accomplished by grouping a number of gloves in a batch to achieve higher manufacturing efficiency. The gloves are immersed in the antimicrobial silver Aloe Vera solution for at least 10 minutes to allow adequate absorbency. Silver containing Aloe Vera is attached to the surface of the glove through a controlled dehydration process. The water in the antimicrobial Aloe Vera solution is caused to evaporate through heating. Although a higher temperature will cause water to evaporate quicker, excess heat may damage the gloves. For example, gloves exposed to excessive heat of over 70° C. may turn brownish and become brittle. To shorten the heat exposure time, a heating oven is preheated to about 45° C. before the gloves are introduced. The oven has a temperature control mechanism to maintain a maximum temperature. In a preferred embodiment the maximum temperature is set at approximately 65° C. and the heating process lasts from about 35 to 40 minutes. The dehydration process provides an affiliation force so that the dry silver (from silver hydrosol) and Aloe Vera can remain associated with the glove surface for an extensive period of time.

Even distribution of the silver hydrosol and Aloe Vera on the glove surface maximizes therapeutic treatment of the hand and minimizes contact between the skin and the glove's composite material. Once this germicidal glove is donned by the user, his or her sweat will mix with the dehydrated layer of antibacterial Aloe Vera, creating a thin film antimicrobial barrier on the skin which will not only allow the glove user to combat potential dermatological problems but it will also help to reduce the risk of cross-contamination of bodily fluids (and associated microorganisms) due to pin hole defects or rips and tears in the gloves which frequently appear during extended use.

Stationary drying is not preferred because the silver hydrosol and Aloe Vera solution tends to flow in the direction of the force of gravity. In a preferred embodiment the heating oven has a device to tumble during the heating to make silver hydrosol and Aloe Vera distribute evenly on the glove surface and to form a uniform antimicrobial coating. Afterward the gloves are cooled to room temperature. The gloves are then inverted so that the surface with the Aloe Vera and dry silver (from silver hydrosol) faces inside.

Antiseptic Hand Soaps. Gels, liquid sprays and sanitizers can also be impregnated with a solution of silver hydrosol with or without dilute hydrogen peroxide to provide one or more of the active disinfectant ingredients. When used in combination with the proper mechanical debridement of the skin, these germicidal/antiseptic solutions can be used to reduce the total of number bacterial and fungal organisms present on the hands and thus lower the incidence of cross-contamination.

Currently, sterile/purified water is mixed with a Mineral Trioxide Aggregate ("MTA") dry powder material to create a colloidal gel like paste which solidifies over time to create a strong impermeable dental barrier material which can be used as a root canal repair material (e.g. "ProRoot MTA root repair material" by Tulsa Dental). However, such a product is highly technique sensitive because it is susceptible to oral contamination by the bacteria in saliva and blood which decrease the likelihood of a successful clinical outcome with the MTA material. The addition of silver hydrosol to the sterile water mixed with the MTA powder provides the colloidal paste material with antimicrobial properties. In fact, the addition of the silver hydrosol is capable of reducing bacterial bio-burden and thus post operative infection and inflammation and therefore it is able to provide a continuous dynamic antimicrobial bacteriostatic environment for the MTA to fully cure (set) resulting in a higher degree of successful root repair.

This antimicrobial version of this MTA material can be used in the following applications:
  a. repair of perforations secondary to internal root resorption;
  b. internal repair of iatrogenic perforations of the tooth crown and/or root (during root canal treatment);
  c. root apexification with or without the use of calcium hydroxide paste;
  d. as a root end filling material; and
  e. sealing off an exposed nerve (pulp capping due to traumatic or carious exposure of the nerve) on either a primary and permanent tooth.

The addition of silver hydrosol to a dilute solution (10-30%) of potassium oxalate and purified water to help reduce sensitivity in teeth to either hot or cold stimulus or to air caused by exposed root (cementum) and/or exposed dentine surfaces. When potassium oxalate combines with the calcium hydroxyapatite minerals in the intratubular dentine of the tooth it forms calcium oxalate crystals which occlude/block the dentinal tubules and reduce the movement of fluid through them. According to the Hydrodynamic Theory of Tooth/pulpal Pain, the reduction in fluid movement reduces nerve stimulus and thus pain. However, there is usually bacterial contamination within these exposed dentinal tubules so the addition of silver hydrosol to the potassium oxalate solution helps provide a continuous dynamic antimicrobial bacteriostatic environment within the dentine capable of reducing bacterial bio-burden and thus post operative sensitivity.

There are also a number of additional Root Canal Products/Applications employing silver hydrosol:
  a. Gutta percha endodontic filling material can be readily impregnated with silver hydrosol similar to the way this same material has previously been impregnated with other antimicrobial agents such as tetracycline or chlorhexidine gluconate. Because silver hydrosol is an antimicrobial metal and not an antimicrobial drug this is a distinctly new and innovative application. The addition of silver hydrosol to the gutta percha material allows for a sustained steady state timed release of silver ions into the surrounding infected tissues providing a continuous dynamic antimicrobial bacteriostatic environment within the dentinal tubules of the root canal system. In those instances where non-vital teeth are associated with apical pathology, the use of an antimicrobial product such as silver hydrosol can help to rapidly lower the bacterial bio-burden and eliminate the area of apical infection. This promotes healing of the surrounding bone and periodontal tissues.

b. An antimicrobial irrigating solution of dilute silver hydrosol with or without dilute hydrogen peroxide for use as an irrigating solution during root canal treatment can be used to reduce the bacterial bio-burden found within the root canal system in either the sclerotic dentinal tubules or the bacterial laden lateral accessory canals. Because silver hydrosol is an antimicrobial metal and not an antimicrobial drug per se, the duration of effective action is much longer without any systemic effects.

c. Antimicrobial Root Canal sealer/cements with the addition of dilute silver hydrosol (for use with either eugenol or non-eugenol based sealer/cement products) are useful with permanent obturation of the root canal following vital pulp-extirpation or permanent obturation of the root canal following removal of infected or necrotic pulp and placement of intra-canal dressings/medicaments. Antimicrobial root canal sealers such as the present invention can be effectively used to reduce the bacterial bio-burden found within the root canal system in either the sclerotic dentine or the bacterial laden lateral accessory canals of non-vital teeth. The addition of silver hydrosol to the a root canal sealer/cement material allows for a sustained steady state timed release of silver ions into the surrounding infected tissues providing for a continuous dynamic antimicrobial bacteriostatic environment within the dentinal tubules of the root canal system. In those instances where non-vital teeth are associated with apical pathology the use of an antimicrobial product such as silver hydrosol can help to rapidly lower the bacterial bio-burden and eliminate the area of apical infection. This promotes healing of the surrounding bone and periodontal tissues. Because silver hydrosol is an antimicrobial metal and not an antimicrobial drug, results are more long lasting without systemic effects.

d. Silver hydrosol allows an Antimicrobial version of Innovative BioCeramix Inc. (IBC's) dental root canal sealer cement called "iRoot SP"—an injectable Root Canal Sealer/Cement. Because iRoot SP does not require any mixing prior to its application to the root canal system, the silver hydrosol can be readily incorporated into the manufacturing process of the iRoot SP product. Indications for this new product include permanent obturation of the root canal following vital pulp extirpation, permanent obturation of the root canal following removal of infected or necrotic pulp and placement of intra-canal dressings. iRoot SP is suitable for use in the lateral, single cone and vertical condensation. Its composition includes Zirconium Oxide, Calcium Silicates, Calcium Phosphate, Calcium Hydroxide, filler, thickening agents AND silver hydrosol. i Root SP is a convenient premixed ready-to-use injectable white hydraulic cement paste which can be used for permanent root canal filling and sealing applications. Insoluble, radiopaque, non-shrinkage during setting with excellent physical and chemical properties. Biocompatible and non-toxic materials based on a bio-ceramic composition. iRoot SP can directly be used for filling root canals with or without the use of gutta percha material. The new antimicrobial version of iRootSP can be effectively used to reduce the bacterial bio-burden found within the root canal system in either the sclerotic dentine or the bacterial laden lateral accessory canals of non vital teeth. The addition of silver hydrosol to the a root canal sealer/cement material allows for a sustained steady state timed release of silver ions into the surrounding infected tissues providing for a continuous dynamic antimicrobial bacteriostatic environment within the dentinal tubules of the root canal system. In those instances where non-vital teeth are associated with apical pathology, the use of an antimicrobial product including silver hydrosol can help to rapidly lower the bacterial bio-burden and eliminate the area of apical infection. This promotes healing of the surrounding bone and periodontal tissues. Because silver hydrosol is an antimicrobial metal and not an antimicrobial, the results are longer lasting without any systemic effects.

e. Silver hydrosol can provide an antimicrobial version of Innovative BioCeramix Inc. (IBC's) Dental root canal filling material called BioAggregate. Silver hydrosol solution which can be readily incorporated into the manufacture of the BioAggregate product. Because silver hydrosol is an antimicrobial metal and not an antimicrobial drug this is a distinctly new and innovative application of an antimicrobial agent which would provide superior results and would not be considered as a readily apparent modification to the original BioAggregate product. Because BioAggregate utilizes the advanced science of nano-technology to produce ceramic particles that, upon reaction with BioA Liquid (deionized water) produce biocompatible and aluminum-free ceramic biomaterials, the Silver hydrosol solution could be readily incorporated into the BioA liquid. When the BioAggregate powder is hydrated, the BioA Liquid precipitates calcium phosphate, which is a component of human bone. During the reaction hydroxyapatite is created and water is formed. The water supplied through this dynamic reaction contributes to the hydration reaction speed, and thus the setting time and strength of BioAggregate. The metallic silver particles of silver hydrosol will not participate in these reactions so the silver particles remain intact and fully functional. When available, the antimicrobial version of BioAggregate product can be used for any of the following applications:
  i. repair of perforations secondary to internal root resorption;
  ii. internal repair of iatrogenic perforations of the tooth crown an or root (during root canal treatment);
  iii. root apexification with out without concomitant use of calcium hydroxide paste;
  iv. root end filling material; and
  v. Sealing an exposed nerve (pulp capping due to traumatic or carious exposure of the nerve) on either a primary or permanent tooth.

In any of the above applications (i.-v.) an antimicrobial version of Bio-Aggregate can be effectively used to reduce the bacterial bio-burden found either within the root canal system or in the surrounding periodontal tissues. The addition of silver hydrosol to this Bio-Aggregate root canal filling material allows for a sustained steady state timed release of silver ions into the surrounding infected tissues providing for a continuous dynamic antimicrobial bacteriostatic environment within the dentinal tubules of the root canal system. In all the above applications the integration of silver hydrosol into this product can help to rapidly lower the bacterial bio-burden and significantly reduce the potential risk of post-operative infection. The presence of the silver hydrosol solution promotes healing of the surrounding bone and periodontal tissues. Because silver hydrosol is an antimicrobial metal and not an antimicrobial drug, effectiveness will be longer with no systemic effects.

The incorporation of silver hydrosol into an auto-cure calcium hydroxide paste creates an antimicrobial version of the product capable of providing continued antimicrobial persistence in the surrounding tissues to which the paste has been applied (especially when the calcium hydroxide paste is being applied as a liner in a deep cavity preparation where there is a possibility that some infected carious dentine still remains). An antimicrobial version of this product can be effectively used to reduce the bacterial bio-burden commonly found within decayed dentinal tubules or sclerotic dentine. The addition of silver hydrosol to this material allows for a sustained steady state timed release of silver ions into the surrounding infected tissues providing for a continuous dynamic antimicrobial bacteriostatic environment within the dentinal tubules of the tooth. This can help to rapidly lower the bacterial bio-burden and to possibly allow for the remineralization of decayed dentine. Because silver hydrosol is an antimicrobial metal and not an antimicrobial drug this is a distinctly new and innovative application with longer effectiveness and absence of systemic effects. Alternatively, an antimicrobial version of this calcium hydroxide paste can be used during a root canal procedure to help stop any residual bleeding while the canal is being dried with absorbable paper points. Since the paste is intended to be left in contact with the tissue until the body metabolizes and excretes it, its antimicrobial features help to decrease inflammation and help with wound healing a the root apex (where the periodontal ligament meets the dentino-cementum junction).

The incorporation of silver hydrosol into an auto-cure or light curable restorative core build-up material creates an antimicrobial version of the product capable of providing continued antimicrobial persistence in the surrounding dentine and enamel hard tissues. Such a product is applied to fill in the voids of a cavity prepared within the tooth and initially has the consistency of a flowable paste which is subsequently cured (either auto cure, light cure or both—"dual cure") and sets to form a permanent material. This material and the surrounding tooth structure is later ground down by the dentist's drill to form the definitive tooth preparation onto which the definitive tooth restoration is later placed. An antimicrobial version of this core build up material has numerous advantages over the prior art since it can be effectively used to reduce the bacterial bio-burden commonly found within decayed dentinal tubules or sclerotic dentine. The addition of silver hydrosol to this material allows for a sustained steady state timed release of silver ions into the surrounding infected tissues providing a continuous dynamic antimicrobial bacteriostatic environment within the dentinal tubules of the tooth. This can help to rapidly lower the bacterial bio-burden and to possibly allow for the remineralization of any remaining decayed or infected dentine. Because silver hydrosol is an antimicrobial metal and not an antimicrobial drug this is a distinctly new and innovative application has longer efficacy than prior art materials without any systemic effects.

Figure 1:
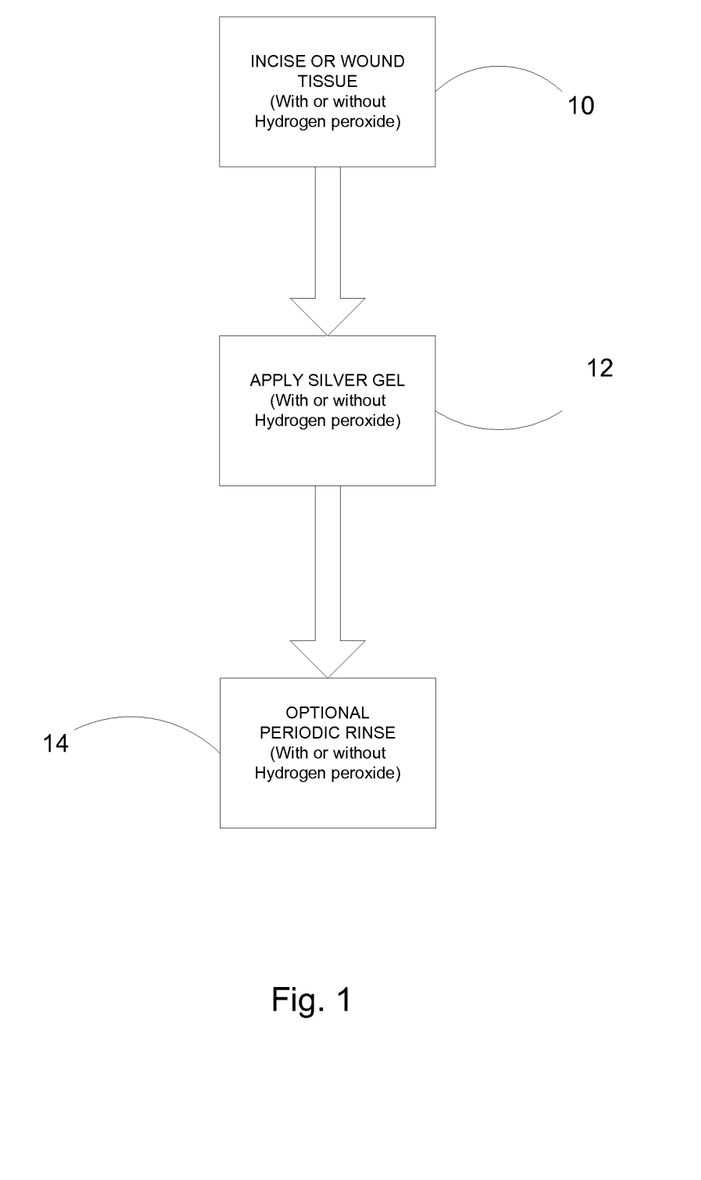
FIG. 1 is a diagram of a first method of the present invention.

The basic steps of our method for reducing pain and swelling in dental procedures are illustrated in FIG. 1. In a first step 10 an incision is made into the gingival tissue as in oral surgery where a flap is cut to remove a tooth, expose the root of a tooth or insert an implant. This step includes other procedures which wound the gingival tissues including gingivoplasty, autologous gingival transplants and gingival retraction cords. In the next step 12 silver hydrosol gel is applied to the wounded tissue. This includes putting the gel under a gingival flap prior to suturing and injecting the gel into gingival pockets. In the final step 14 the patient's mouth is periodically rinsed with a solution containing silver hydrosol to disinfect the wounded surface. Rinsing is optimally carried out at least three times per day for at least several days. A ten day duration of the periodic rinsing is preferred. The preferred rinsing solution contains silver hydrosol combined with diluted hydrogen peroxide.

Figure 2:
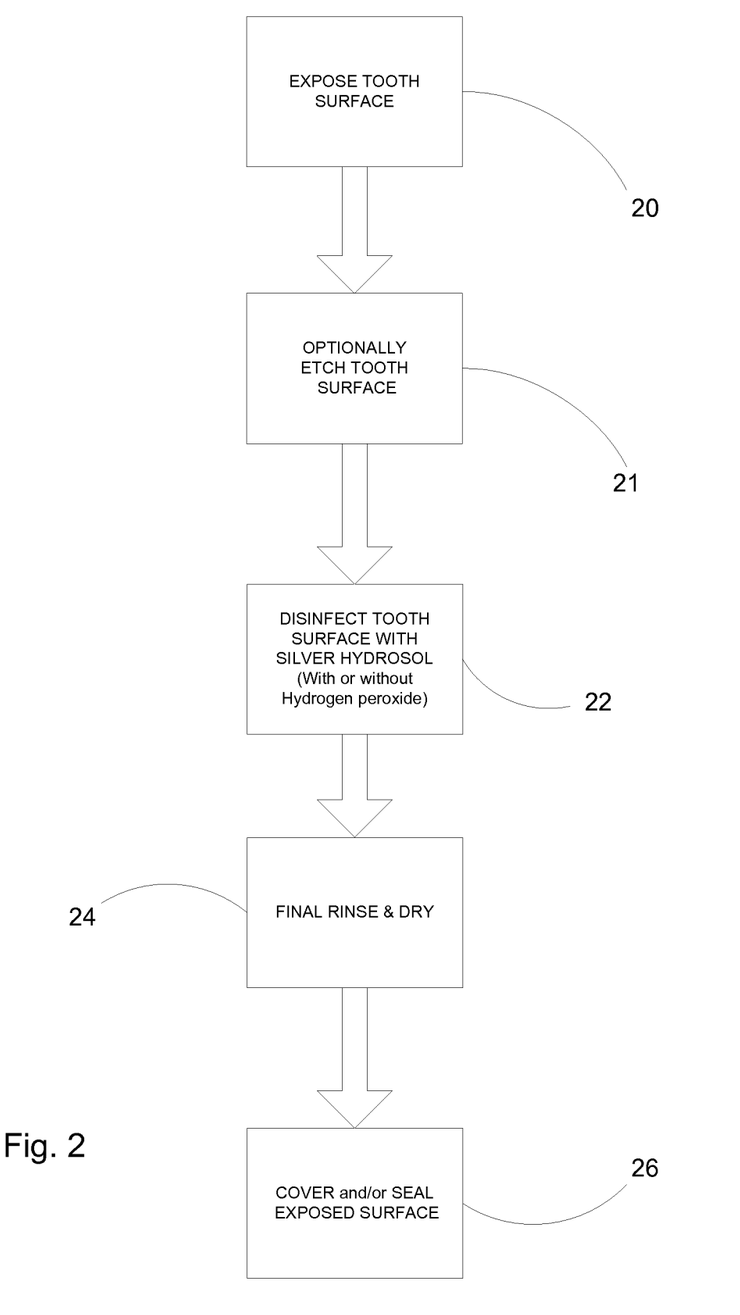
FIG. 2 is diagram of a second method of the present invention.

FIG. 2 shows our method for disinfecting tooth preparation prior to applying restorative materials (fillings) or permanent crowns. In a first step 20 an internal tooth surface is exposed by removing a temporary crown, an old restoration or an area of decay. In a second step 22 the entire exposed tooth surface is disinfected with a solution containing silver hydrosol and hydrogen peroxide. In step 24 the exposed tooth surface is given a rinse with a silver hydrosol solution and air dried. Alternatively, the final rinse could be with sterile water or the surface can be dried following the disinfection. In a final step 26 the restorative material or permanent crown is applied to cover and protect the exposed internal surface.

There are also several non-dental applications for this solution of electrolytic silver hydrosol solution combined with dilute hydrogen peroxide, as it can also be used as a skin body wash/disinfectant rinse to help debride skin lesions and sores such as chronic decubatous ulcers and other bacterial/fungal infections of the skin. This type of antimicrobial skin wash can create a continuous dynamic antimicrobial bacteriostatic environment capable of reducing bacterial bio-burden as well as post operative infection and inflammation. This in turn, results in reduced healing times and post operative discomfort.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method for reducing pain, swelling infection resulting from dental procedures comprising the steps of:
    making an incision into or a wound in gingival or dental tissue within the mouth of a patient;
    applying a gel containing a silver metal particle hydrosol to the incision or the wound; and
    rinsing the mouth periodically with an aqueous rinse solution containing a silver metal particle hydrosol rinse solution to reduce the bio-burden thereby reducing pain and swelling or infection resulting from dental procedures.

2. The method according to claim 1, wherein the aqueous rinse solution contains at least 5 ppm silver metal.

3. The method according to claim 1, wherein the aqueous rinse solution further comprises hydrogen peroxide.

4. The method according to claim 3, wherein the hydrogen peroxide is present at a concentration of at least 1.5% hydrogen peroxide by weight.

5. The method according to claim 1, wherein the step of rinsing is repeated multiple times daily.

6. The method according to claim 5, wherein the step of rinsing is repeated over a seven to ten day period.

7. The method according to claim 6, wherein the seven to ten day period is either reduced or extended depending on the patient's symptoms and post-operative response.

8. The method according to claim 1, wherein the step of making includes forming a flap of gingival tissue and the step of applying includes applying the gel under the flap prior to suturing the flap.

9. The method according to claim 1, wherein the step of applying includes applying the gel into and around extraction sockets immediately after tooth removal.

10. The method according to claim 1, wherein the step of applying includes flushing the gel into gingival pockets following scaling or gingival curettage.

11. The method according to claim 10, wherein the gel further comprises hydrogen peroxide.

12. A method for reducing tooth sensitivity following dental restorative procedures comprising the steps of:
- creating an exposed surface on a tooth;
- disinfecting the exposed surface with a solution containing silver metal particle hydrosol; and
- covering the exposed surface with a restorative material.

13. The method according to claim 12, wherein the solution further comprises hydrogen peroxide.

14. The method according to claim 12, further comprising a step of sealing the surfaces of the tooth.

15. The method according to claim 14, wherein the step of sealing comprises applying an endodontic sealing and filling material.

16. The method according to claim 15, wherein the endodontic sealing and filling material comprises a root canal sealer/cement and a gutta percha filling material.

17. The method according to claim 12, further comprising a step of etching the surface of the tooth following the step of creating.

18. The method according to claim 12 further comprising a step of rinsing the tooth following the step of disinfecting.

19. The method according to claim 18 further comprising the step of using silver hydrosol solution as a rinse solution.

20. The method according to claim 18 further comprising the step of using silver metal particle hydrosol solution containing hydrogen peroxide as a rinse solution.

21. The method according to claim 12, wherein the step of covering includes applying a crown to the exposed surface.

22. The method according to claim 1, further comprising a step of closing the incision or the wound.

\* \* \* \* \*